(12) United States Patent
Musa et al.

(10) Patent No.: US 8,557,226 B2
(45) Date of Patent: Oct. 15, 2013

(54) PERFORMANCE-BOOSTING UV-ABSORBING COMPOUNDS

(75) Inventors: Osama M. Musa, Hillsborough, NJ (US); Jenn S. Shih, Paramus, NJ (US)

(73) Assignee: ISP Investments Inc., Wilmington, DE (US)

(*) Notice: Subject to any disclaimer, the term of this patent is extended or adjusted under 35 U.S.C. 154(b) by 573 days.

(21) Appl. No.: 12/688,980

(22) Filed: Jan. 18, 2010

(65) Prior Publication Data
US 2010/0183532 A1 Jul. 22, 2010

Related U.S. Application Data

(60) Provisional application No. 61/145,268, filed on Jan. 16, 2009.

(51) Int. Cl.
*A61K 8/44* (2006.01)
*A61K 8/49* (2006.01)
*C07D 207/40* (2006.01)

(52) U.S. Cl.
USPC ............. 424/59; 424/60; 548/520; 548/546

(58) Field of Classification Search
USPC ................... 424/59, 60; 548/520, 546
See application file for complete search history.

(56) References Cited

U.S. PATENT DOCUMENTS

| | | |
|---|---|---|
| 2,961,347 A | 11/1957 | Floyd |
| 3,227,615 A | 1/1966 | Korden |
| 3,428,589 A | 2/1969 | Coats |
| 3,589,578 A | 6/1971 | Kamphausen |
| 4,077,411 A | 3/1978 | Ward |
| 4,077,441 A | 3/1978 | Rosen et al. |
| 4,131,576 A | 12/1978 | Iovine et al. |
| 4,850,517 A | 7/1989 | Ter Stege |
| 4,857,596 A | 8/1989 | MacLeay et al. |
| 4,868,246 A | 9/1989 | MacLeay et al. |
| 6,255,405 B1 | 7/2001 | Kang et al. |
| 6,492,455 B1 | 12/2002 | Nadolsky |
| 7,361,710 B2 | 4/2008 | Thames et al. |
| 2005/0191249 A1 | 9/2005 | Bonda et al. |
| 2008/0081059 A1 | 4/2008 | Narayanan et al. |

FOREIGN PATENT DOCUMENTS

WO PCT/EP2007/051697 2/2007

OTHER PUBLICATIONS

Aydin, S., et al., "The effects of anhydride type and amount on viscosity and film properties of alkyd resins," *Prog Org Coat*, 51, 273-279, 2004.
Billingham, N.C., *Molar Mass Measurements in Polymer Science*, Halsted Press, 1979.
Billmeyer, F., *Textbook of Polymer Science*, Wiley Interscience, 1984.
Grob, R.L., and Barry, E.F., *Modern Practice of Gas Chromatography, third edition*, John Wiley & Sons, 1995.
Guner, F.S., et al., "Polymers from triglyceride oils," *Prog Polym Sci*, 31, 633-670, 2006.
Schroder, E., et al., *Polymer Characterization*, Hanser Publishers, 1989.
Silverstein, R.M., et al., *Spectrometric Identification of Organic Compounds*, John Wiley & Sons, 1981.
Yoder, C.H. and Schaeffer Jr., C.D., *Introduction to Multinuclear NMR*, The Benjamin/Cummings Publishing Company, Inc., 1987.

*Primary Examiner* — James O Wilson
*Assistant Examiner* — Ebenezer O Sackey
(74) *Attorney, Agent, or Firm* — William J. Davis

(57) ABSTRACT

UV-absorbing compounds are disclosed that are derived from at least: (a) a UV absorber having at least one hydroxyl group, primary amine group, or secondary amine group, (b) a coupling agent having anhydride functionality, and (c) a graft host comprising an unsaturated fatty acid. These compounds absorb, scatter, deflect, or scatter ultraviolet radiation in a variety of personal care and performance chemical applications.

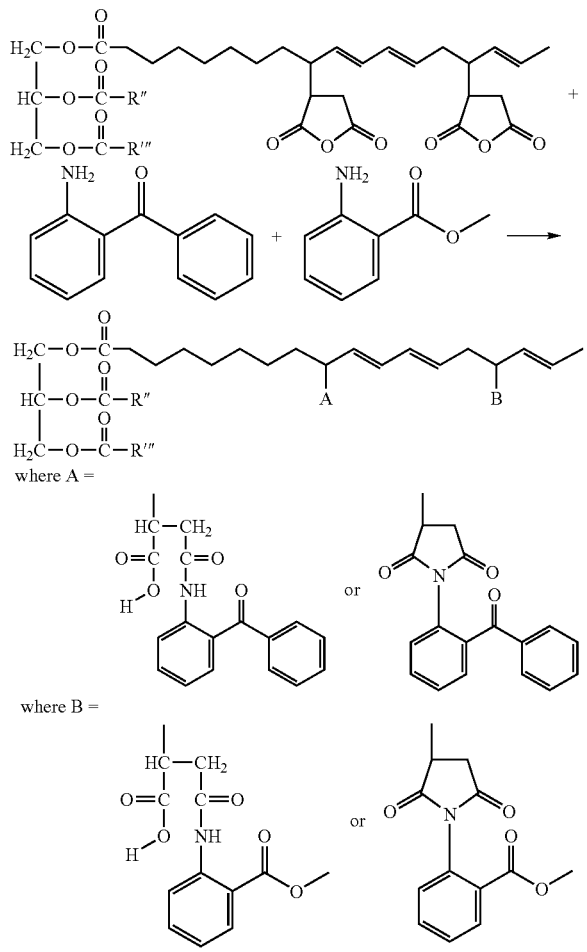

R" and R'" are alkyl or alkenyl groups that naturally occur in oil.

7 Claims, No Drawings

PERFORMANCE-BOOSTING UV-ABSORBING COMPOUNDS

FIELD OF THE INVENTION

The disclosed invention relates to compositions that boost the performance of ultraviolet (UV) absorbers, comprising (a) a UV absorber having at least one hydroxyl group, primary amine group, or secondary amine group, (b) a coupling agent having anhydride functionality, and (c) a graft host comprising an unsaturated fatty acid. Such performance-boosting compositions enable novel formulations for absorbing, reflecting, and/or scattering radiation.

In preferred embodiments, the UV absorber exhibits UV-A activity, UV-B activity, or both UV-A and UV-B activity, the coupling agent is maleic anhydride, and the graft host is an unsaturated oil or unsaturated fat. The compositions may be employed in personal care and industrial applications.

DESCRIPTION OF RELATED ART

It is now generally accepted that ultraviolet (UV) radiation can be a serious health hazard. Even a limited exposure to solar radiation can cause short- and long-term skin damage, such as erythema, burns, wrinkles, lentigo ("liver spots"), skin cancers, keratotic lesions, and other cellular changes. There is a greater risk for developing such conditions for those who send prolonged time in the sun, such as for their occupation or during recreation.

UV radiation is just one portion of the electromagnetic spectrum with wavelengths from about 100 nm and about 400 nm, and is further divided into three subregions. UV-A radiation, from about 320 nm to about 400 nm, has the longest wavelength within the UV spectrum, and consequently is the least energetic. While UV-A rays can induce skin tanning, they are liable to induce adverse changes as well, especially in the case of sensitive skin or of skin which is continually exposed to solar radiation. In particular UV-A rays cause a loss of skin elasticity and the appearance of wrinkles, leading to premature skin aging. UV-B rays have shorter wavelengths, from about 290 nm to about 320 nm, and their higher energy can cause erythema and skin burns which may be harmful. The third subgroup, UV-C has the shortest wavelengths, from about 200 nm to about 290 nm, and the highest energy. The Earth's ozone layer effectively filters much UV-C radiation from reaching the ground. Nonetheless, UV-C rays can be generated from tanning bed devices.

In addition to harming the skin, UV radiation can injure the hair, resulting in color changes (especially for color-treated hair), embrittlement, and a loss in aesthetics (e.g., shine, manageability).

UV radiation damage is not limited to the skin and hair, as inanimate objects exposed to solar radiation can experience changes related to color, hardness, and structural integrity, which can contribute to aesthetical and functional deterioration. Thus, there is the very real and demanding need for compositions that protect the skin, hair, and objects from UV rays, especially UV-A and UV-B radiation. Of special interest are compositions that provide broad UV-spectrum protection from both UV-A and UV-B radiation.

Broadly speaking, para-aminobenzoic acid (PABA) exhibits a common trait shared with many UV absorbers/filters. The molecule possesses both electron withdrawing and electron accepting groups, providing resonance delocalization that coincides with the absorbed energy of UV radiation:

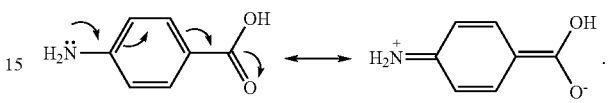

However, PABA is a highly polar molecule, making it water soluble, and giving it low persistence, meaning that it is not highly retained on the skin after swimming or perspiring. In addition, due to extensive intermolecular bonding, PABA exists as a solid, which may further complicate its formulation. Thus, there exists the need to improve the persistence of UV absorbers, especially those that are water-soluble, and to provide formulation flexibility.

UV absorbers may exhibit photolability, in which the absorbed energy causes photodegradation and/or photoreactivity, and thus reduce its efficacy. Such photolability may result from irreversible isomerisms keto-enol tautomerism and cis-trans isomerism), photocleavage, and/or photoaddition, and may be formulation sensitive, (e.g., blends of avobenzone and octinoxate). Examples of photolabile UV absorber include, without limitation: avobenzone, PABA derivatives, cinnamates, and dibenzoyl methane derivatives, all of which degrades over time, and reduce UV protection. Hence, there exists a need to stabilize UV absorbers from photodegradative effects.

Additionally, there exists the need to enhance the efficacy of UV absorbers without increasing their content in the formula, since a maximum addition level frequently is regulated. This efficacy need is especially important for avobenzone, a highly effective UV-A absorber. Avobenzone is subject to keto-enol isomerization due to formulation dependencies (e.g., solvent, other UV absorbers):

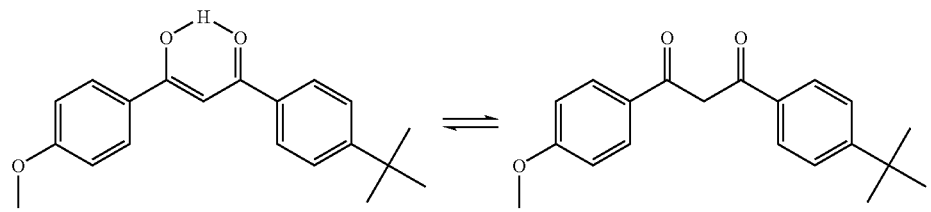

The enol tautomer (left) has its maximum absorbance at 357 nm, which identifies it as a UV-A absorber. Unfortunately, avobenzone is subject to bimolecular reactions (viz, via cleavage mechanisms) that alter the molecule's structure and decrease its effectiveness as an UV absorber. Hence, an effective method is needed for stabilizing labile UV absorbers like avobenzone in order to enhance their efficacy without increasing their addition level.

Methods for stabilizing UV absorbers, and in particular UV absorbers, are known in the prior art. For example, in U.S.

Pat. No. 4,868,246 teaches polymer chemistries having UV absorbers bonded to recurring units:

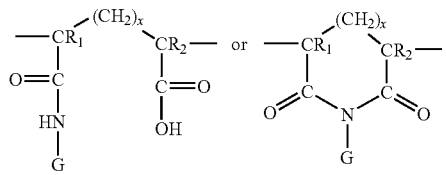

in the polymer backbone, on grafted side chains, as pendant units, or as combinations thereof. The group N-G is the residue of a primary amino or hydrazido substituted stabilizer group selected from (a) 2-hydroxybenzophenones, (b) 2-(2-hydroxyphenyl)-2H-benzotriazoles, (c) aryl salicylates, or (d) oxalic acid amides. A number of potential maleic anhydride polymers are potential stabilizers for the UV absorbers, and include: (a) styrene-maleic anhydride, (b) alternating copolymers of maleic anhydride and alpha-olefins, (c) alkyl vinyl ethers and maleic anhydride, (d) maleic anhydride modified polyolefins, (e) maleic anhydride adducts of hydrogenated polymers or copolymers, and (f) maleic anhydride adducts of EPDM. The '246 patent exclusively teaches polymeric compositions, and does not contain reference to UV absorber bound to a graft host via an anhydride coupling agent.

A similar approach is taught in U.S. Pat. No. 4,857,596 for thermally stabilizing antioxidants.

Two radiation-absorbing polymer chemistries are taught in U.S. Pat. No. 6,255,405. The '405 patent is directed toward radiation-absorbing compositions and coatings, particular for "forming a bottom anti-reflective coating upon producing an integrated circuit." The polymeric compositions comprise two recurring units, the first having the formula:

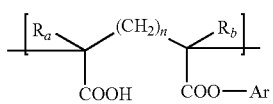

wherein $R_a$ and $R_b$ may be the same or different and represent hydrogen, an alkyl group or other organic groups, Ar represents an organic UV absorber, and n represents 0 or an integer of 1 or more; and the second recurring unit having the formula:

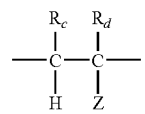

wherein $R_c$ and $R_d$ may be the same or different and each represents hydrogen, an alkyl group, a carboxyl group, or other organic groups, and Z represents hydrogen, a substituted or non-substituted alkoxyl group, a substituted or non-substituted alkyl group, a halogen atom, —CN, an alkylcarbonyloxy group, an imide group, a substituted or non-substituted carbamoyl group, a substituted or non-substituted oxycarbonyl group, or a substituted or non-substituted phenyl group.

The '405 patent recognizes the use of its UV absorber compounds only for electrical circuit board applications.

U.S. Pat. No. 6,492,455 discloses compositions comprising the reaction product of a $C_6$+ alpha olefin/maleic anhydride copolymer with a polyfunctionalized secondary or tertiary amine. The resulting copolymer is an alternating copolymer of an olefinic monomer and a maleic anhydride with a polyfunctionalized secondary or tertiary amine. Uses includes hair spray and water-proof sunscreen compositions U.S. Pat. No. 7,361,710 describes compositions comprising the reaction of (a) an unsaturated vegetable oil and an enophile or dienophile having acid, ester, or anhydride functionality and (b) a functional vinyl monomer. For example, soybean oil is reacted with maleic anhydride through an ene grafting reaction, to yield a maleated vegetable oil:

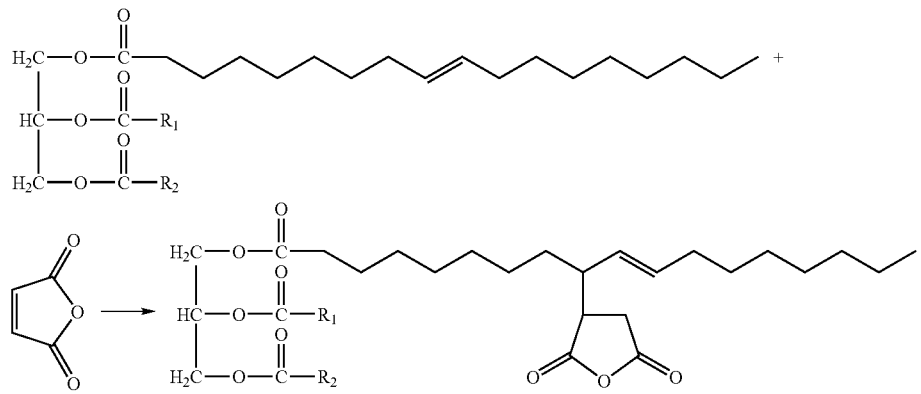

The maleated oil is reacted with hydroxyethyl methacrylate, 2-(tert-butylamino)ethyl methacrylate, or glycidyl methacrylate.

Another maleated oil is described in U.S. Pat. No. 3,428,589, which is directed to polycarboxylic acid anhydride resins of high viscosity, and for such resins of voltage capabilities. This invention discloses the heating (1) of a thy oil, a modified drying oil, or a mixture thereof, and (2) and alpha, beta-ethylenically unsaturated dicarboxylic acid anhydride, which is heated until a polycarboxylic acid anhydride resin product (i.e., an adduct) with a desirably high viscosity is obtained. The polycarboxylic acid anhydride resin is then reacted with an organic aromatic primary or secondary amine, as represented in the following reaction:

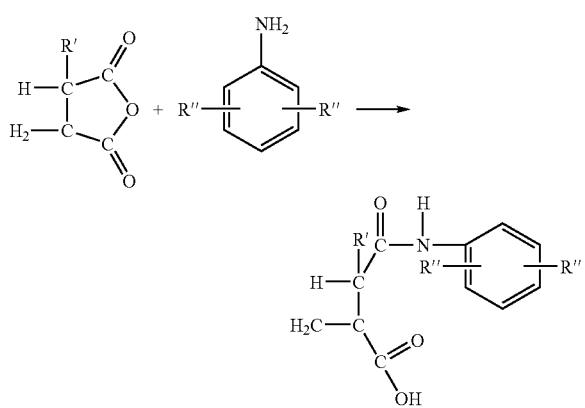

wherein R' represented the drying oil portion of the adduct, and R" is hydrogen or alkyl. The '589 patent specifies that the organic aromatic primary or secondary amine has from 1 to 20 carbon atoms, preferably from 1 to 10 carbon atoms. The '589 patent discloses compositions for electrocoating baths, compositions with high throwing power, and of excellent intermediate voltage capacity.

Additional disclosure related to anhydride-functionalized vegetable oils is provided by Aydin, S., et al., *Prog Org Coat*, 51, 273-279, 2004; and by Guner, F. S., et al., *Prog Polym Sci*, 31, 633-670, 2006, both of which are incorporated in their entirety by reference. While these works describe methods to graft anhydride functional groups onto vegetable oils, they do not teach subsequent grafting of UV absorbers onto the anhydride moiety.

Functionalized poly(alpha olefin-maleic anhydride) polymers are the subject of application PCT/EP2007/051697. This functionalized copolymer has the structure:

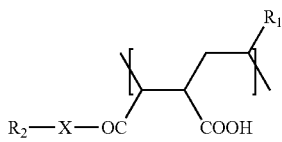

wherein X is —O— or —NH—, and —X—R$_2$— is a functional radical selected from a group that includes natural molecules that are UV absorbers, such as tannins, flavonoids, thymol, caffeic acid esters, and vitamin E.

Despite advances in designing UV absorbers and in developing formulation blends, there remains a commercial demand for UV absorber compositions with boosted performance, especially for single compositions that provide full UV-spectrum protection, enhanced water-resistance, reduced tendency for skin penetration, and improved stability especially for labile IN absorbers. The compositions disclosed herein uniquely accomplish these properties.

SUMMARY OF THE INVENTION

It has been discovered that performance-boosting UV absorber compounds can be derived from at least (a) one UV absorber having at least one hydroxyl group, primary amine group, or secondary amine group, (b) a coupling agent having anhydride functionality, and (c) a graft host comprising an unsaturated fatty acid. Such compositions can be produced via three routes, the preferred being that at least one UV absorber is reacted with the preformed ene grafting reaction product between a molecule having anhydride functionality and a graft host comprising an unsaturated fatty acid. The UV absorber compounds can be produced with or without added reaction solvent, initiator, or catalyst, or blends thereof.

In preferred embodiments, the coupling agent is maleic anhydride.

In other preferred embodiments, the graft host comprising an unsaturated fatty acid is an unsaturated liquid oil or an unsaturated solid fat.

In especially preferred embodiments, the ene grafting reaction product is an unsaturated maleated vegetable oil.

In another embodiment of the invention, the UV absorber is a UV absorber, and in preferred embodiments, the UV absorber exhibits at least one of UV-A or UV-B absorption activity. In especially preferred embodiments, the UV absorber comprises at least one UV-A active and at least one UV-B active, being provided by one or more UV absorbers.

These UV absorber compounds exhibit better resistance (permanence), and offer customizable UV spectrum protection. A result of formulation flexibility in selecting the fatty acid, the skin penetration of the UV absorbers may be reduced or essentially eliminated. Remarkably, single molecular entities are produced that offer both UV-A and UV-B protection, providing enhanced UV protection while simultaneously reducing formulary burden. Even more surprisingly, labile UV absorbers, such as avobenzone, may be stabilized when blended with these UV absorber compounds, thus further increasing their use as well.

In a preferred embodiment, the UV absorber compounds are used in personal care applications. In especially preferred embodiments, the UV absorber compounds are used in sun-care formulations.

In other preferred embodiments, the performance-boosting UV absorber compounds are used in non-personal care applications, such as adhesives, coatings, construction materials, encapsulations, ink, printing, plastics, or packaging applications.

DETAILED DESCRIPTION OF THE DISCLOSED EMBODIMENTS

The terms "ultraviolet" and "UV" are taken to mean electromagnetic radiation, especially solar electromagnetic radiation, with a wavelength from about 100 nm to about 400 nm, and includes the UV-A, UV-B, and UV-C subclassifications of such radiation.

The term "UV-A" means ultraviolet electromagnetic radiation with a wavelength from about 320 nm to about 400 nm, and includes UV-A1 (from about 340 nm to about 400 nm) and UV-A2 (from about 320 nm to about 340 nm).

The term "UV-B" means ultraviolet electromagnetic radiation with a wavelength from about 290 nm to about 320 nm.

The term "UV-C" means ultraviolet electromagnetic radiation with a wavelength from about 200 nm to about 290 nm.

The term "UV absorber" means compositions that absorb, reflect, and/or scatter UV radiation.

Personal care compositions refers to such illustrative non-limiting compositions as skin, sun, oil, hair, cosmetic, and preservative compositions, including those to alter the color and appearance of the skin. Other personal care compositions are those that enhance flexibility in styling, durable styling, increased humidity resistance for hair, skin, and color cosmetics, sun care water-proof/resistance, wear-resistance, and thermal protecting/enhancing compositions.

The term "sun-care formulation" means personal care and/or pharmaceutical formulations comprising an effective amount of UV-absorbing compounds. Sun-care formulations include beach and non-beach products that are applied to the face, décolleté, lips, and skin to treat and/or protect against erythema, burns, wrinkles, lentigo ("liver spots"), skin cancers, keratotic lesions, and cellular changes of the skin; and to hair to treat and/or protect against color changes, lack of luster, tangles, split ends, unmanageability, and embrittlement.

The term "performance chemicals application" refers to any application that is not a personal care or pharmaceutical application. Examples of performance chemicals applications include, but are not limited to: adhesive, agricultural, cleaning, coating, construction material, encapsulation, ink, membrane, personal care, printing, plastic, or packaging composition.

All percentages, ratio, and proportions used herein are based on a weight basis unless other specified.

It has been discovered that performance-boosting UV absorber compounds are provided by compounds derived from at least (a) a UV absorber having at least one hydroxyl group, primary amine group, or secondary amine group, (b) a coupling agent having anhydride functionality, and (c) a graft host comprising an unsaturated fatty acid. Such compositions can be produced via three pathways, the preferred being that the UV absorber is reacted with an ene graft reaction product between a molecule having anhydride functionality and a graft host comprising an unsaturated fatty acid. The UV absorber compounds can be produced with or without added reaction solvent, initiator, or catalyst, or blends thereof.

In preferred embodiments, coupling agent is maleic anhydride.

In addition to treating and/or protecting from the effects of radiation absorption, these compositions do not suffer UV absorber loss by volatilization, migration, or extraction, even at high temperatures, because the UV absorber is covalently bonded. As a direct consequence, the performance of products made with the invention's compositions are enhanced.

UV Absorber

The first required reactant is at least one UV absorber. Preferred UV absorbers are those that exhibit UV-A activity, UV-B activity, or both UV-A and UV-B activity. Due to the wide array of potential UV-active chemistries, it is appreciated that a select number is suitable for human use, while a many of the other UV absorber chemistries find industrial use, e.g., in adhesives, coatings, encapsulations, inks, lacquers, packaging, paints, plastics, and varnishes. It is outside the scope of this invention to specify all such actives in each application field, especially UV absorbers approved for human use in different countries. Rather, this invention recognizes the specific reactive chemistries necessary to produce the claimed compositions.

The UV absorbers of this invention exhibit at least one hydroxyl, primary amine, or secondary amine functionality. These specific functional groups are indicated as they open the ring structure of the graft host.

Non-limiting examples of UV absorbers that exhibit the necessary hydroxyl, primary amine, or secondary amine functionalities include:

p-aminobenzoic acid and its derivatives: 4-aminobenzoic acid (PABA); digalloyl triolate; 2,3-dihydroxypropyl 4-aminobenzoate (lisadimate, amyl dimethyl PABA, glyceryl PABA); ethyl-4-bis(hydroxypropyl)-aminobenzoate (roxadimate); ethoxylated ethyl 4-aminobenzoate (PEG-25 PABA); hexyl 2-[4-(diethylamino)-2-hydroxybenzoyl]benzoate (diethylamino hydroxy benzoyl hexylbenzoate); (5-methyl-2-propan-2-ylcyclohexyl) 2-aminobenzoate (menthyl anthranilate, meradimate);

benzophenone derivatives: (2-hydroxy-4-methoxyphenyl)-(2-hydroxyphenyl)methanone (dioxybenzone, benzophenone-8); 2,2',4,4'-tetrahydroxybenzophenone (benzophenone-2, Uvinul® D-50); 2-hydroxy-4-methoxybenzophenone (oxybenzone, benzophenone-3); 2,2'-dihydroxy-4,4'-dimethoxybenzophenone (benzophenone-6); 2,2'-dihydroxy-4,4'-dimethoxybenzophenone-5,5'-disulphonic acid sodium salt (benzophenone-9); 4-hydroxy-2-methoxy-5-(oxo-phenylmethyl)benzenesulfonic acid (sulisobenzone, benzophenone-4); 2-hydroxy-4-methoxybenzophenone-5-sulphonic acid sodium salt (benzophenone-5), 2-aminobenzophenone; (2-hydroxy-4-(octyloxy)phenyl) phenylmethanone; 2,2,4,4-tetramethyl-7-oxa-3,20-diazadispiro (5.1.11.2)heneicosan-21-one, benzotriazole derivatives: 2-(benzotriazol-2-yl)-6-[[3-(benzotriazol-2-yl)-2-hydroxy-5-(2,4,4-trimethylpentan-2-yl)phenyl]methyl]-4-(2,4,4-trimethylpentan-2-yl)phenol (bisoctrizole); 2-(2-hydroxy-5-methylphenyl)benzotriazole (drometrizole); 2-(2H-benzotriazol-2-yl)-4-methyl-6-[2-methyl-3-(1,3,3,3-tetramethyl-1-((trimethylsilyl)oxy)disiloxanyl)propyl]phenol (drometrizole trisiloxane): 2,2'-methylenebis-[4-(1,1,3,3-tetramethylbutyl)-6-(2H-benzotriazol-2-yl)phenol](methylene bis-benzotriazolyl tetramethylbutylphenol); 2-(2H-benzotriazole-2-yl)-4-(1,1,3,3-tetramethylbutyl)-phenol (Uvinul® 3029, Uvinul® 3029 GR);

benzimidazole derivatives: 2-phenylbenzimidazole-5-sulfonic acid and its potassium, sodium and triethanolamine salts, (phenylbenzimidazole sulfonic acid, ensulizole); phenylene)bis-1Hbenzimidazole-4,6-disulfonic acid, monosodium salt (disodium phenyl dibenzimidazole tetrasulfonate);

camphor derivatives: α-(2-oxoborn-3-ylidene)-toluene-4-sulphonic acid and its salts (benzylidene camphor sulfonic acid); 3,3'-(1,4-phenylenedimethylene)bis(7,7-dimethyl-2-oxobycyclo-[2.2.1]hept-1-ylmethane sulphonic acid and its salts (terephthalylidene dicamphor sulfonic acid, emcamsule); polymer of N-{(2 and 4)-[(2-oxoborn-3-ylidene)methyl]benzyl}(polyacrylamido methylbenzylidene camphor);

cinnamates: diethanolamine-p-methoxycinnamate (DEA methoxycinnamate);

quinones: lawsone with dihydroxyacetone;

salicylates: 2-ethylhexyl salicylate (ethylhexyl salicylate); 3,3,5-trimethylcyclohexyl salicylate (homosalate, homomethyl salicylate); 2-(bis(2-hydroxyethyl)amino)ethyl 2-hydroxybenzoate (trolamine salicylate, triethanol amine salicylate);

triazine derivatives: 2,4,6-trianilino-(p-carbo-2'-ethylhexyl-1'-oxy)-1,3,5-triazine (ethylhexyl triazone); 4,4'-[[6-[[[(1,1-dimethylethyeamino]carbonyl]phenyl]amino]-1,3,5-triazine-2,4-diyl]diimino]bis-bis(2-ethylhexyl)benzoate (diethylhexyl butamido triazone, iscotrizinol); 2,2'-[6-(4-methoxyphenyl)-1,3,5-triazine-2,4-diyl]bis[5-[(2-ethylhexyl)oxy]phenol (bis-ethylhexyloxyphenol methoxyphenyl triazine); and 2,2'-[6-(4-methoxyphenyl)-1,3,5-triazine-2,4-diyl]bis{5-[(2-ethylhexyl)oxy]phenol}(bemotrizinol, Tinosorb® S).

Examples of UV absorbers having the necessary hydroxyl, primary amine, or secondary amine functionalities include, without limitation:

amines: bis-benzoxazoyl phenyl ethylhexyl amino triazine; N,N'-bisformyl-(2,2,6,6-tetramethyl-4-piperidinyl)-hexamethylendiamine (Uvinul® 40450 H); bis-(2,2,6,6-tetramethyl-4-piperidyl)-sebacate (Uvinul® 4077 H and 4077 GR); sterically hindered oligomeric amine, CAS number 152261-33-1 (Uvinul® 5050 H); N,N'-bisformyl-N,N'-bis- (2,2,6,6-tetramethyl-4-piperidinyl)-hexamethylendiamine (Uvinul® 4050 H); N-(2-ethoxyphenyl)-Y-(2-ethylphenyl)oxamide benzoates: methyl-2-aminobenzoate;

benzophenones: beta-2-glucopyranoxypropylhydroxybenzophenone; [2-hydroxy-4-(octyloxy)phenyl](phenyemethanone (Uvinul® 3008 and 3008 FL);

benzotriazoles: 6-tert-butyl-2-(5-chloro-2H-benzotriazole-2-yl)-4-methylphenol (Uvinul® 3026 and 3026 GR); 2,4-di-tent-butyl-6-(5-chloro-2H-benzotriazole-2-yl)-phenol (Uvinul® 3027); 2-(2H-benzotriazole-2-yl)-4,6-di-tert-pentylphenol (Uvinul® 3028 and 3028 GR); 2-(2H-benzotriazole-2-yl)-4-methylphenol (Uvinul® 3033 P); 2-(2H-benzotriazole-2-yl)-4,6-bis(1-methyl-1-phenylethyl)phenol (Uvinul® 3034); 4-methylhexyl 3-(3-benzotriazol-2-yl-4-hydroxy-5-tert-butyl-phenyl)propanoate;

cinnamates: (E)-3-(4-hydroxy-3-methoxyphenyl)prop-2-enoic acid (ferulic acid);

salicylates: 2-[bis(2-hydroxyethyl)amino]ethyl salicylate; and triazones: 2-[p-(tert-butylamido)-anilino]-4,6,-bis[(p-(2F-ethylhexyl-1'-oxycarbonyl)-anilino]-1,3,5-triazine.

The abovementioned UV absorbers at least one hydroxyl, primary amine, or secondary amine group and generally contain 10 carbon atoms or more, preferably containing 20 carbon atoms or more.

Preferred embodiments of this invention that are UV-A actives include, but not limited to: 2-aminobenzophenone, bemotrizinol, bis-benzoxazoyl phenyl ethylhexyl amino triazine, bisoctrizole, diethylaminohydroxybenzoylhexylbenzoate, diethylhexyl butamido triazone, dioxybenzone, disodium phenyl dibenzimidazole tetrasulfonate, drometrizole trisiloxane, ecamsule, ensulizole, menthyl anthranilate, meradimate, oxybenzone, sulisobenzone, and blends thereof.

Preferred embodiments of this invention that are UV-B actives include, but not limited to: aminobenzoic acid, amyl dimethyl PABA, benzophenone-9,3-benzylidene camphor sulfonic acid, bisoctrizole, camphor benzalkonium methosulfate, diethanolamine p-methoxycinnamate, diethylhexyl butamido triazone, digalloyl trioleate, drometrizole trisiloxane, ensulizole, ethyl 4-bis(hydroxypropyl)aminobenzoate, ethylhexyl p-methoxycinnamate, 2-ethylhexyl salicylate, ethylhexyl triazone, glyceryl aminobenzoate, homomethyl salicylate, lawsone with dihydroxyacetone, meradimate, methoxycinnamido propyl hydroxy sultaine, oxybenzone (benzophenone-3), 2-phenylbenzimidazole-5-sulfonic acid (and its potassium, sodium and triethanolamine salts), sulisobenzone (benzophenone-4), triethanolamine salicylate, and blends thereof.

In especially preferred embodiments of this invention, performance-boosting UV absorber compounds comprise at least one UV-A active and at least one UV-B active. This is to say that at least one UV-A active and at least one UV-B active are grafted onto the same or different graft host compounds. Within the context of this embodiment, it is especially preferred that at least one UV-A active and at least one UV-B active are grafted onto the same graft host compound to create a compound having both UV-A and UV-B absorbing activity.

Anhydride Coupling Agent

In the present invention at least one anhydride coupling agent is provided, which serves as a covalent bond agent between the UV absorber and the graft host that comprises an unsaturated fatty acid.

There are two forms that the anhydride coupling agent assumes. In one form the anhydride coupling agent has a carbon-carbon double bond that is able to graft to unsaturated fatty acid through an ene addition reaction. Non-limiting examples of this form of the anhydride coupling agent include: maleic anhydride, dimethyl maleic anhydride, itaconic anhydride, and citraconic anhydride, their derivatives, and blends thereof.

Alternatively, the anhydride coupling agent is the above-described anhydride coupling agent after the ene grafting reaction with the graft host. In this form, the original carbon-carbon double bond is replaced with a carbon-carbon single bond, and the anhydride coupling agent and the graft host are one molecule. Non-limiting examples of this form of the anhydride coupling agent include: succinic anhydride and its derivatives. Note that although the anhydride coupling agent in this form may be "succinic anhydride," it is common to refer to the ene grafted reaction product as "maleated," e.g., "maleated oil."

In preferred embodiments, the anhydride coupling agent is maleic anhydride (first described form) and succinic anhydride adduct (second described form).

Graft Host Comprising an Unsaturated Fatty Acid

Another reactant to produce the UV absorber-absorbing compound is a graft host comprising an unsaturated fatty acid. Prior to the addition of the anhydride coupling agent, the graft host must comprise at least one carbon-carbon double bond in order to enable the ene grafting reaction. As such, the graft host comprises at least one unsaturated fatty acid prior to the ene reaction. However, after ene grafting reaction, it is possible to hydrogenate the reaction product to partially or completely saturate any remaining alkenyl groups.

Unsaturated fatty acids are those compounds described by the structure:

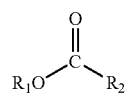

wherein $R_1$ is hydrogen or the residue product from the esterification of glycerol, and $R_2$ is an alkenyl chain. Fatty acids may be attached to other molecules, producing molecules known as "fats" and "oils," and unattached to other molecules, in which case they are called, "free fatty acids." Free fatty acids that exist in nature are termed, "natural fatty acids."

Natural fatty acids contain as few as 4 carbons (butyric acid) and as many as 28 carbons (caprylic acid) or more. Many such natural unsaturated fatty acids are known, and include: arachidonic acid, cervonic acid, clupanodinic acid, docosahexaenoic acid, eicosenoic acid, eicosapentaenoic acid, elaidic acid, crude acid, gadoleic acid, hepatodecenoic acid, linoleic acid, conjugated linoleic acid, alpha-linoleic acid, gamma linolenic acid, dihomo-gamma-linoleic acid, myristoleic acid, oleic acid, palmitoleic acid, ricinoleic acid, timnodonic acid, vaccenic acid, and vernolic acid, and blends thereof.

As an alternative to free fatty acids, the graft host may take the form of a liquid-state oil, a soft-state butter, or a solid-state fat, or blends thereof. One common feature among these forms is that they are esterification product of three fatty acids with glycerol, which is known by the generic name triglyceride and the following structure:

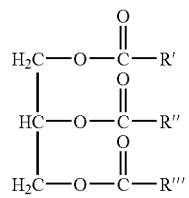

wherein R', R", and R'" independently are alkyl or alkenyl groups, one of which must be an alkenyl group. The state of matter for triglycerides depends on the nature of R', R", and R'", and increasing fatty acid chain lengths enhances molecular entanglements, increases the melting point, increases hydrophobicity, and decreases penetration into porous substrates. Oils, butters, and fats find application in this invention provided they are exist in a liquid state during the reaction, e.g., solidified fats can be liquefied by heating them.

One non-limiting example of an unsaturated oil is soybean oil, which is composed of five major fatty acids: palmitate, stearate, oleate, linolenate, and linoleate. Hence, soybean oil may be represented by the following molecule, which is derived from linolenate, linoleate, and palmitate fatty acids:

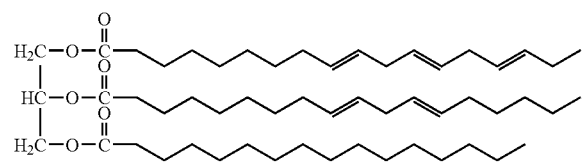 [SMILES: CC/C=C/C/C=C/C/C=C/CCCCCCCC(=O)OCC(COC(=O)CCCCCCCCCCCCCCC)OC(=O)CCCCCCC/C=C/C/C=C/CCCCC]

Unsaturated butters and fats from animal and plant origin also are known, and include, without limitation: cocoa butter, illipe butter, milk butter, shea butter, and mango butter and blends thereof. Likewise, unsaturated animal and plant fats are known, and include, without limitation: beef fat, chicken fat, Japan wax, lards, mutton fat, pig fat, suets, and tallows.

Of course, many natural oils and fats are known.

Due to the inherent complexity of naturally-occurring materials, many oils and fats contain a multiplicity of fatty acids and fat molecules. The only limitation in their suitability is that they comprise at least 1 unsaturated carbon-carbon bond for the ene grafting reaction to take place.

Additionally, natural and synthetic fats, such as triglycerides, can be synthesized in the laboratory in the reaction between free fatty acids and glycerol Synthesis of the UV Absorber Compound Three methods are provided for the production of the UV absorber compounds of this invention.

The first method is preferred, comprising the reaction of at least two reactants: (a) the first of which is a UV absorber having at least one hydroxyl group, primary amine group, or secondary amine group, and (b) the second of which is a preformed ene grafting reaction product between an anhydride coupling agent and a graft host comprising an unsaturated fatty acid. The reactive UV absorber is grafted onto the anhydride moiety by ring opening of the anhydride.

A preferred compound comprising a maleated unsaturated fatty acid is a maleated vegetable oil, as described in U.S. Pat. No. 7,361,710. Maleated oils are favored in the current invention, as they demonstrate low toxicity, sustainable production, and contribute to improved persistence (water resistance) of the UV absorber compound. Maleated forms of unsaturated vegetable oils, include, but not limited to: almond, castor, corn, cottonseed, linseed, mineral, olive, palm kernel, peanut, rapeseed, rice bran oil, sesame, soybean, sunflower, and their derivatives, and blends thereof.

The UV absorber compounds of this invention may be produced via a second method, which comprises at least three reactants: (a) a UV absorber comprising hydroxyl group, primary amine group, and/or secondary amine group, (b) a coupling agent comprising anhydride functionality, and (c) a graft host comprising an unsaturated fatty acid. The UV absorber reacts with the coupling agent to open the anhydride ring. That reaction product is then grafted onto the compound comprising an unsaturated fatty acid via an ene addition reaction.

Alternatively, the UV absorber compounds may be produced by a third method, which also comprises at least three reactants: (a) a UV absorber having at least one hydroxyl group, primary amine group, or secondary amine group, (b) a coupling agent having anhydride functionality, and (c) a graft host comprising an unsaturated fatty acid. The coupling agent participates in an ene reaction with the graft host. Then, the UV absorber opens the anhydride ring to yield the final UV absorber product.

It is within the scope of this invention to employ mixtures of UV absorbers (e.g., UV-A and UV-B absorbers). It may be advantageous to add the least reactive UV absorbers first, and the more reactive ones later in the preparation.

Alternately, multiple UV absorbers can be blended together and used. Regardless of the type or number of UV absorbers, their total molar equivalents should not exceed the equivalents of the anhydride moiety in the coupling agent. As necessary, additional reactive species can be attached to the composition. To properly adjust the stoichiometry of multiple reactive additives, the relative anhydride content must be considered.

The use of certain reactants and selection of reaction temperature may result in a reacting system of high viscosity, which may reduce the reaction yield. A resolution to this problem is the addition of an optional reaction solvent. The reaction comprising the UV absorber and the graft host may be carried out without or with added inert solvents, including: benzene, toluene, xylene, mesitylene, chlorobenzene, dimethylformamide, tetrahydrofuran, aliphatic hydrocarbons, and the Ceraphyl® emollients product line of International Specialty Products (Wayne, N.J.), such as diisopropyl adipate (Ceraphyl® 230).

In some cases the reaction may stop at the intermediate amic acid form, with partial or complete conversion of the amic acid to the cyclic imide form may occur. Such conversion may occur if the reaction temperature is sufficiently high, viz. above 225° C., or during an optional heat treatment, e.g., to reduce residual monomer concentration. Alternatively, catalyst may be added to the reaction to facilitate this form conversion.

For example, a product of this invention, which comprises the UV-B absorber 2-aminobenzoate, can be converted from its amic acid to imide form by heating, using a catalyst, or a combination of both:

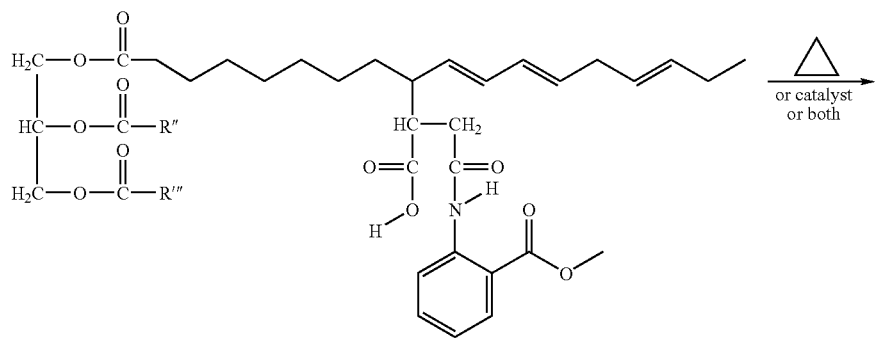

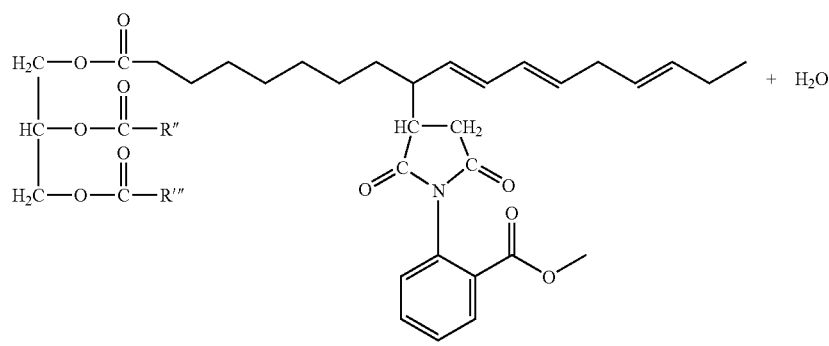

The reaction may be carried out for times ranging from 30 seconds to 48 hours or even more, depending upon (a) the degree of conversion to imide form that is desired, (b) the reactivity of the UV absorbers, (c) the reaction temperature employed, (d) the presence or absence of a solvent, and (e) the use or non-use of an initiator and/or catalyst. With the use of an optional reaction solvent or solvents, it may be preferred to remove the solvent(s) after the reaction, e.g., at reduced pressure and/or elevated temperature, and then to add a different solvent conducive to the final formulation. Applying a vacuum may further help to reduce the residual concentration (s) of the UV absorber(s).

Typically, the temperature ranges from 20° C. to the decomposition temperature of any reactant. At lower reaction temperatures, UV absorber bearing primary and/or secondary amine group may become attached to the anhydride coupling agent as amic acid derivatives. During high-temperature processing, such and amic acid form will tend to cyclize to the imide form.

Since the UV absorber actives are covalently bonded to the anhydride-comprising graft host, they are not lost from the reacted product by volatilization, migration, or other mechanisms even at high temperatures. As a result, the compositions of this invention are particularly useful for extended product service life. Any unreacted (residual) UV absorber may be removed using methods known in the art. For example, when the UV absorber has a lower boiling point than the final product, the graft host, or the ene-graft reacted graft host, then distillation (e.g., vacuum distillation or thin film distillation) may be used.

The UV absorbing compounds of this invention are useful in personal care products, sun-care products, and in performance chemicals applications, including polymers and inks that otherwise degrade when exposed to solar radiation. Also contemplated is the use of the disclosed UV absorbing compounds to protect wood, lignin, and foliage from UV damage.

The performance-boosting UV absorber compounds of this invention can be used together with other additives to further enhance the properties of the finished product. Examples of other additives that can be used in conjunction with the stabilizers of this invention include antioxidants, e.g., alkylated monophenols, alkylated hydroquinones, hydroxylated thiodiphenyl ethers, alkylidene-bis-phenols, hindered phenolic benzyl compounds, acylaminophenols, esters of 3-(3,5-di-tent-butyl-4-hydroxyphenyepropionic acid, esters of 3-(5-tert-butyl-4-hydroxy-3-methylphenyl) propionic acid, 3-(3,5-di-tert-butyl-4-hydroxyphenyl)propionic acid amides; and other additives.

Optional: Initiator

An optional free radical initiator may be added to the reactants to graft the cited UV absorber onto the graft host. Advantages of using an optional initiator(s) may include lower reaction temperatures and/or more complete extent of reaction.

Compounds capable of initiating the free-radical polymerization include those materials known to function in the prescribed manner, and include the peroxo and azo classes of materials. Exemplary peroxo and azo compounds include, but are not limited to: acetyl peroxide; azo bis-(2-amidinopropane) dihydrochloride; azo bis-isobutyronitrile; 2,2'-azo bis-(2-methylbutyronitrile); benzoyl peroxide; di-tert-amyl peroxide; di-tert-butyl diperphthalate; butyl peroctoate; tert-butyl dicumyl peroxide; tert-butyl hydroperoxide; tert-butyl perbenzoate; tert-butyl permaleate; tert-butyl perisobutylrate; tert-butyl peracetate; tert-butyl perpivalate; para-chlorobenzoyl peroxide; cumene hydroperoxide; diacetyl peroxide; dibenzoyl peroxide; dicumyl peroxide; didecanoyl peroxide; dilauroyl peroxide; diisopropyl peroxodicarbamate; dioctanoyl peroxide; lauroyl peroxide; octanoyl peroxide; succinyl peroxide; and bis-(ortho-toluoyl) peroxide.

Also suitable to initiate the free-radical polymerization are initiator mixtures or redox initiator systems, including: ascorbic acid/iron(II) sulfate/sodium peroxodisulfate, tert-butyl hydroperoxide/sodium disulfite, and tert-butyl hydroperoxide/sodium hydroxymethanesulfinate.

Optional: Additional Formulation Ingredients and Adjuvants

Optional additional formulation ingredients and adjuvants may be incorporated with the performance-boosting UV absorber compounds described herein. Such ingredients may be incorporated without altering the scope of the current invention, and may be included in order to produce formulated products intended for end-use applications, including those for personal care and performance chemical applications such as coatings, packaging, personal care, pharmaceutical items, plastics, and printing.

The composition of the invention also can contain one or more additional cosmetically acceptable additives chosen from conditioning agents, protecting agents, such as, for example, hydrosoluble, antiradical agents, antioxidants, vitamins and pro-vitamins, fixing agents, oxidizing agents, reducing agents, dyes, cleansing agents, anionic, cationic, nonionic and amphoteric surfactants, thickeners, perfumes, pearlizing agents, stabilizers, pH adjusters, filters, preservatives, hydroxy acids, cationic and nonionic polyether associative polyurethanes, polymers other than the cationic polymer described herein, vegetable oils, mineral oils, synthetic oils, polyols such as glycols and glycerol, silicones, aliphatic alcohols, colorants, bleaching agents, highlighting agents and sequestrants. These additives are present in the composition according to the invention in proportions that may range from 0 to 20% by weight in relation to the total weight of the composition. The precise amount of each additive may be easily determined by an expert in the field according to its nature and its function.

Any known conditioning agent is useful in the personal care compositions of this invention. Conditioning agents function to improve the cosmetic properties of the hair, particularly softness, thickening, untangling, feel, and static electricity and may be in liquid, semi-solid, or solid form such as oils, waxes, or gums. Similarly, any known skin altering agent is useful in the compositions of this invention. Preferred conditioning agents include cationic polymers, cationic surfactants and cationic silicones.

Conditioning agents may be chosen from synthesis oils, mineral oils, vegetable oils, fluorinated or perfluorinated oils, natural or synthetic waxes, silicones, cationic polymers, proteins and hydrolyzed proteins, ceramide type compounds, cationic surfactants, fatty amines, fatty acids and their derivatives, as well as mixtures of these different compounds.

The synthesis oils include polyolefins, e.g., poly-α-olefins such as polybutenes, polyisobutenes and polydecenes. The polyolefins can be hydrogenated.

The mineral oils suitable for use in the compositions of the invention include hexadecane and oil of paraffin.

A list of suitable animal and vegetable oils comprises sunflower, corn, soy, avocado, jojoba, squash, raisin seed, sesame seed, walnut oils, fish oils, glycerol tricaprocaprylate, Purcellin oil or liquid jojoba, and blends thereof.

Suitable natural or synthetic oils include eucalyptus, lavender, vetiver, litsea cubeba, lemon, sandalwood, rosemary, chamomile, savory, nutmeg, cinnamon, hyssop, caraway, orange, geranium, cade, and bergamot.

Suitable natural and synthetic waxes include carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The cationic polymers that may be used as a conditioning agent according to the invention are those known to improve the cosmetic properties of hair treated by detergent compositions. The expression "cationic polymer" as used herein, indicates any polymer containing cationic groups and/or ionizable groups in cationic groups. The cationic polymers used generally have a molecular weight the average number of which falls between about 500 and 5,000,000 and preferably between 1000 and 3,000,000.

The preferred cationic polymers are chosen from among those containing units including primary, secondary, tertiary, and/or quaternary amine groups that may either form part of the main polymer chain or a side chain.

Useful cationic polymers include known polyamine, polyaminoamide, and quaternary polyammonium types of polymers, such as:

(1) homopolymers and copolymers derived from acrylic or methacrylic esters or amides. The copolymers can contain one or more units derived from acrylamides, methacrylamides, diacetone acrylamides, acrylamides and methacrylamides, acrylic or methacrylic acids or their esters, vinyllactams such as vinyl pyrrolidone or vinyl caprolactam, and vinyl esters. Specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name Gafquat® by International Specialty Products; the dimethyl amino ethyl methacrylate/vinyl caprolactam/vinyl pyrrolidone terpolymers, such as the product sold under the name Gaffix® VC 713 by International Specialty Products; the vinyl pyrrolidone/methacrylamidopropyl dimethylamine copolymer, marketed under the name Styleze® CC 10 by International Specialty Products; and the vinyl pyrrolidone/quaternized dimethyl amino propyl methacrylamide copolymers such as the product sold under the name Gafquat® HS 100 by International Specialty Products (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as the hydroxy alkyl cellulose, and the hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.
(7) derivatives of polyamino amides resulting from the condensation of polyalcoylene polyamines with polycarboxylic acids followed by alcoylation by bi-functional agents.
(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers are described in U.S. Pat. Nos. 3,227,615 and 2,961,347.
(9) the cyclopolymers of alkyl dialyl amine or dialkyl diallyl ammonium such as the homopolymer of dimethyl diallyl ammonium chloride and copolymers of diallyl dimethyl ammonium chloride and acrylamide.
(10) quaternary diammonium polymers such as hexadimethrine chloride.
(11) quaternary polyammonium polymers, including, for example, Mirapol® A 15, Mirapol® AD1, Mirapol® AZ1, and Mirapol® 175 products sold by Miranol.
(12) the quaternary polymers of vinyl pyrrolidone and vinyl imidazole such as the products sold under the names Luviquat® FC 905, FC 550, and FC 370 by BASF Corp. (Ludwigshafen, Del.).
(13) quaternary polyamines.
(14) reticulated polymers known in the art.

Other cationic polymers that may be used within the context of the invention are cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

Preferred cationic polymers are derivatives of quaternary cellulose ethers, the homopolymers and copolymers of dimethyl diallyl ammonium chloride, quaternary polymers of vinyl pyrrolidone and vinyl imidazole, and mixtures thereof.

The conditioning agent can be any silicone known by those skilled in the art to be useful as a conditioning agent. The silicones suitable for use according to the invention include polyorganosiloxanes that are insoluble in the composition. The silicones may be present in the form of oils, waxes, resins, or gums. They may be volatile or non-volatile. The silicones can be selected from polyalkyl siloxanes, polyaryl siloxanes, polyalkyl aryl siloxanes, silicone gums and resins, and polyorgano siloxanes modified by organofunctional groups, and mixtures thereof.

Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes preferably having a number-average molecular weight between 200,000 and 1,000,000, used alone or mixed with a solvent. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxy-silicate type.

The organo-modified silicones suitable for use in the invention include silicones such as those previously defined and containing one or more organofunctional groups attached by means of a hydrocarbon radical and grafted siliconated polymers. Particularly preferred are amino functional silicones.

The silicones may be used in the form of emulsions, nano-emulsions, or micro-emulsions.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one $C_1$-$C_{18}$ alkyl.

Hydrolyzed proteins include Croquat L, in which the quaternary ammonium groups include a $C_{12}$ alkyl group, Croquat M, in which the quaternary ammonium groups include $C_{10}$-$C_{18}$ alkyl groups, Croquat S in which the quaternary ammonium groups include a $C_{18}$ alkyl group and Crotein Q in which the quaternary ammonium groups include at least one $C_1$-$C_{18}$ alkyl group. These products are sold by Croda.

The conditioning agent can comprise quaternized vegetable proteins such as wheat, corn, or soy proteins such as cocodimonium hydrolyzed wheat protein, laurdimonium hydrolyzed wheat protein and steardimonium hydrolyzed wheat protein.

2-N-stearoyl amino-o ctadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl) amide of cetylic acid, N-docosanoyl N-methyl-D-glucamine and mixtures of such compounds.

The conditioning agent can be a cationic surfactant such as a salt of a primary, secondary, or tertiary fatty amine, optionally polyoxyalkylenated, a quaternary ammonium salt, a derivative of imadazoline, or an amine oxide. Suitable examples include mono-, di-, or tri-alkyl quaternary ammonium compounds with a counterion such as a chloride, methosulfate, tosylate, etc. including, but not limited to, cetrimonium chloride, dicetyldimonium chloride, behentrimonium methosulfate, and the like. The presence of a quaternary ammonium compound in conjunction with the polymer described above reduces static and enhances combing of hair in the dry state. The polymer also enhances the deposition of the quaternary ammonium compound onto the hair substrate thus enhancing the conditioning effect of hair.

The conditioning agent can be any fatty amine known to be useful as a conditioning agent; e.g. dodecyl, cetyl or stearyl amines, such as stearamidopropyl dimethylamine.

The conditioning agent can be a fatty acid or derivatives thereof known to be useful as conditioning agents. Suitable fatty acids include myristic acid, palmitic acid, stearic acid, behenic acid, oleic acid, linoleic acid, and isostearic acid. The derivatives of fatty acids include carboxylic ester acids including mono-, di-, tri- and tetra-carboxylic acids.

The conditioning agent can be a fluorinated or perfluorinated oil. The fluoridated oils may also be fluorocarbons such as fluoramines, e.g., perfluorotributylamine, fluoridated hydrocarbons, such as perfluorodecahydronaphthalene, fluoroesters, and fluoroethers.

Of course, mixtures of two or more conditioning agents can be used.

The conditioning agent or agents can be present in an amount of 0.001% to 20%, preferably from 0.01% to 10%, and even more preferably from 0.1% to 3% by weight based on the total weight of the final composition.

The composition of the invention can contain one or more protecting agents to prevent or limit the degrading effects of natural physical and/or chemical assaults on the keratinous materials.

The antioxidants or antiradical agents can be selected from phenols such as BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, and lactoferrin.

The vitamins can be selected from ascorbic acid (vitamin C), vitamin E, vitamin E acetate, vitamin E phosphate, B vitamins such as B3 and B5, vitamin PP, vitamin A, and derivatives thereof. The provitamins can be selected from panthenol and retinal.

The protecting agent can be present in an amount 0.001% to 20% by weight, preferably from 0.01% to 10% by weight, and more preferably 0.1 to 5% by weight of the total weight of the final composition.

In addition, the compositions according to the invention advantageously include at least one surfactant, which can be present in an amount of 0.1% and 60% preferably 1% and 40%, and more preferably 5% and 30% by weight based on the total weight of the composition. The surfactant may be chosen from among anionic, amphoteric, or non-ionic surfactants, or mixtures of them known to be useful in personal care compositions.

Additional thickeners or viscosity increasing agents may be included in the composition of the invention, such as: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/$C_{10}$-$C_{30}$ alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus* gummifer gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; coco-betaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; nano gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cyclonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa* multiflora flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia urens gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides and *zea mays* (corn) starch.

Preferred thickeners or viscosity increasing agents include carbomer, aculyn and Stabileze®, e.g. crosslinked acrylic acid, crosslinked poly(methylvinyl ether/maleic anhydride) copolymer, acrylamides, carboxymethyl cellulose and the like.

The compositions according to the invention may be used to wash and treat keratinous material such as hair, skin, eyelashes, eyebrows, fingernails, lips, and hairy skin.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

The compositions of the invention may also take the form of skin-washing compositions, and particularly in the form of solutions or gels for the bath or shower, or of make-up removal products.

The compositions of the invention may also be in the form of aqueous or hydro-alcoholic solutions for skin and/or hair care.

The compositions according to the invention can be detergent compositions such as shampoos, bath gels, and bubble baths. In this mode, the compositions will comprise a generally aqueous washing base. The surfactant or surfactants that form the washing base may be chosen alone or in blends, from known anionic, amphoteric, or non-ionic surfactants. The quantity and quality of the washing base must be sufficient to impart a satisfactory foaming and/or detergent value to the final composition. The washing base can be from 4% to 50% by weight, preferably from 6% to 35% by weight, and even more preferentially from 8% to 25% by weight of the total weight of the final composition.

With respect to personal care products, additional formulation ingredients of particular interest are those selected from the list comprising: anti-oxidants, bronzing/self-tanning agents, colorants, defoamers, emollients, fragrances, humectants, insect repellants, lower monoalcohols, lower polyols, micro- and nano-particulate UV absorbents, moisturizers, pigments, preservatives, propellants, oils, surfactants, thickeners, water, and waxes.

With respect to coatings, packaging, plastics, and/or printing product, additional formulation ingredients of particular interest are selected from the list comprising: colorants, defoamers, dyes, fragrances, lacquers, lakes, latexes, micro- and nano-particulate UV absorbents, pigments, plasticizers, preservatives (including biocides), solvents, surfactants, thickeners, varnishes, and water.

Product Forms

The UV absorbing compounds of this invention find use in a large number of product forms. In one embodiment, the UV absorber compound takes the form of a film, e.g., applied neat or from a solvent-evaporation step. In preferred embodiments, the UV absorbing compounds are employed in personal care, sun-care, or performance chemicals formulations.

Personal care compositions according to the invention may, for example, be used as care and/or sun protection product for the face and/or the body having a consistency ranging from liquid to semiliquid (e.g., milks, creams), and gels, creams, pastes, powders (including compacted powders), and wax-like compositions.

For compositions intended to protect the hair from UV radiation, suitable product forms include, but not limited to: conditioners, dispersions, emulsions, gels, lotions, mists, mousses, shampoos, and sprays.

Optionally, formulations comprising the UV absorber compound may be packaged as an aerosol and may be provided in the form of a mousse or a spray. It may be advantageous to utilize known propellants (e.g., hydrofluorinated compounds dichlorodifluoromethane, difluoroethane, dimethyl ether, isobutene, N-butane, propane, trichlorofluoromethane) to aide in their delivery.

In a different embodiment, compositions of this invention may be provided in the form of vaporizable fluid lotions to be applied to the skin or the hair. Pressurized devices are a suitable means for vaporizing fluid lotions, and are known to one skilled in the art. For example, they are described in U.S. Pat. Nos. 4,077,441 and 4,850,517.

The UV absorbing compounds may be formulated for performance chemical applications, e.g., be provided in a form suitable for brush or roller coating of wood surfaces and substrates, or provided in an atomizable form for spraying plants, trees, and crops. Selection of the graft host comprising an unsaturated fatty acid can influence the properties of the final formulation, for example, viscosity and penetration characteristics.

Formulating the compounds of the invention as a stable microemulsion in water may be accomplished using the method taught in US patent application 2008/0081059, the entire contents of which are hereby incorporated by reference.

Due to the great potential for controlling the anhydride and UV absorber addition levels, the product may comprise from about 0.01% to about 100% of the described UV absorber compound.

Characterizing of the Product

The characterization of the UV absorber compound can be analyzed by known techniques. Especially preferred are the techniques of $^{13}$C nuclear magnetic resonance (NMR) spectroscopy, gas chromatography (GC), and gel permeation chromatography (GPC) in order to decipher polymer identity, residual UV-A and UV-B concentrations, polymer molecular weight and polymer molecular weight distribution.

Nuclear magnetic resonance (NMR) spectroscopy is an especially preferred method to probe the polymerization product in terms of chemical properties such as monomeric composition, sequencing and tacticity. Analytical equipment suitable for these analyses include the Inova 400-MR NMR System by Varian Inc. (Palo Alto, Calif.). References broadly describing NMR include: Yoder, C. H. and Schaeffer Jr., C. D., *Introduction to Multinuclear NMR*, The Benjamin/Cummings Publishing Company, Inc., 1987; and Silverstein, R. M., et al., *Spectrometric Identification of Organic Compounds*, John Wiley & Sons, 1981, which are incorporated in their entirety by reference.

Residual reactant levels can be measured by GC, which can be used to indicate the extent of reactant conversion by the polymerization process. GC analytical equipment to perform these tests are commercially available, and include the following units: Series 5880, 5890, and 6890 GC-FID and GC-TCD by Agilent Technologies, Inc. (Santa Clara, Calif.). GC principles are described in *Modern Practice of Gas Chromatography, third edition* (John Wiley & Sons, 1995) by Robert L. Grob and Eugene F. Barry, which is hereby incorporated in its entirety by reference.

GPC is an analytical method that separates molecules based on their hydrodynamic volume (or size) in solution of the mobile phase, such as hydroalcoholic solutions with surfactants. GPC is a preferred method for measuring polymer molecular weight distributions. This technique can be performed on known analytical equipment sold for this purpose, and include the TDAmax™ Elevated Temperature GPC System and the RImax™ Conventional Calibration System by Viscotek™ Corp. (Houston, Tex.). In addition, GPC employs analytical standards as a reference, of which a plurality of narrow-distribution polyethylene glycol and polyethylene oxide standards representing a wide range in molecular weight is the preferred. These analytical standards are available for purchase from Rohm & Haas Company (Philadelphia, Pa.) and Varian Inc. (Palo Alto, Calif.). GPC is described in the following texts, which are hereby incorporated in their entirety by reference: Schroder, E., et al., *Polymer Characterization*, Hanser Publishers, 1989; Billingham, N.C., *Molar Mass Measurements in Polymer Science*, Halsted Press, 1979; and Billmeyer, F., *Textbook of Polymer Science*, Wiley Interscience, 1984.

The invention will now be described with reference to the following examples:

EXAMPLES

Maleation Reaction 1

Grafting Maleic Anhydride onto Soybean Oil without Initiator

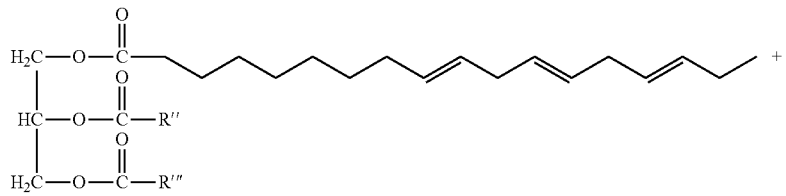

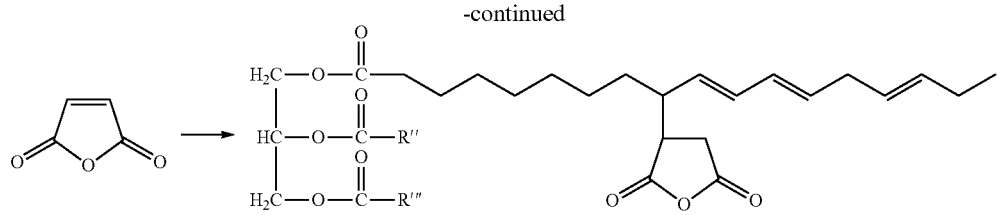

R″ and R‴ are alkyl or alkenyl groups that naturally occur in soybean oil.

Into a 1-L, 4-necked kettle equipped with a thermocouple, a condenser, a nitrogen purge adaptor, and a mechanical stirrer, 391 g soybean oil and 109 g of maleic anhydride were charged. The mixture temperature was slowly raised over 30 minutes from room temperature (about 22° C.) to 210° C., and then held isothermally for about 5-6 hours. Completion of the reaction was indicated when a drop of the reacting solution did not turn triphenylphosphine test paper orange-red in color.

Example 1

Grafting a UV-B Absorber onto Maleated Soybean Oil (without Initiator)

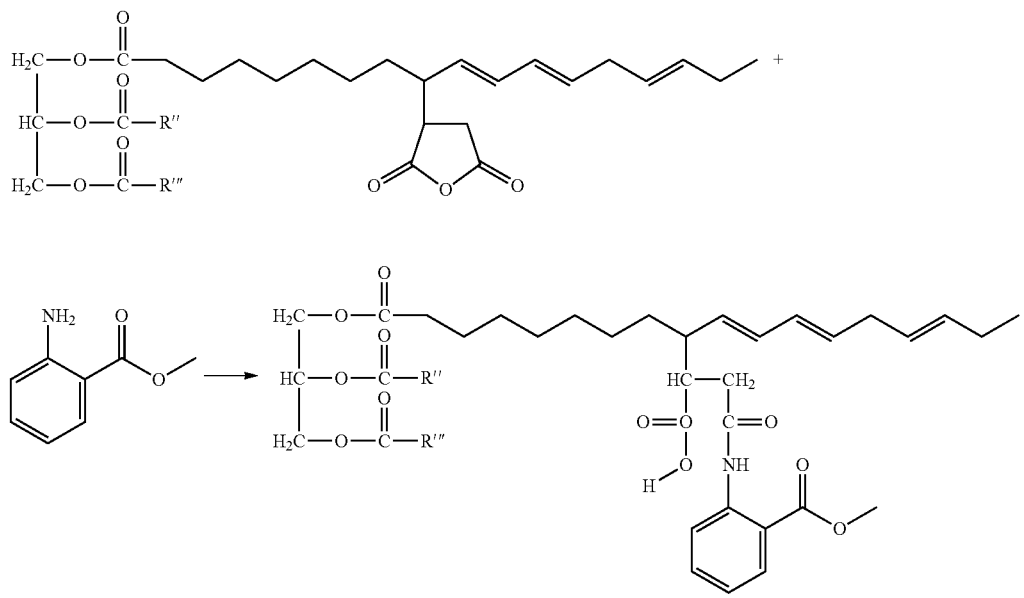

R″ and R‴ are alkyl or alkenyl groups that naturally occur in soybean oil.

In a 1-L, 4-necked kettle equipped with a thermocouple, a condenser, a nitrogen purge adaptor, and a mechanical stirrer, 100 g of Maleination Reaction I product and 30 g of methyl-2-aminobenzoate, a UV-B absorber, were mixed and heated to 80° C. and held for 21 hours.

Maleination Reaction 2

Grafting Maleic Anhydride onto Soybean Oil with Initiator

In a 1-L, 4-necked kettle equipped with a thermocouple, a condenser, a nitrogen purge adaptor, and a mechanical stirrer, 400 g soybean oil were charged. The mixture was heated to 130° C. under nitrogen purge, and held isothermally for 30 minutes. Then, 6.0 g of di-tent-butyl peroxide (DTPO) were charged, and then 6.67 g of maleic anhydride were charged every 10 minutes over the course of 1 hour (total amount of maleic anhydride charged: 40 g). Thirty minutes later, another 6.0 g of DTPO were charged to the vessel. The reactor was held isothermally at 130° C. for about 5-6 hours. Completion of the reaction was indicated when a drop of the reacting solution failed to turn triphenylphosphine test paper orange-red.

Example 2

Grafting a UV-B Absorber onto Maleated Soybean Oil (with Initiator)

In a 1-L, 4-necked kettle equipped with a thermocouple, a condenser, a nitrogen purge adaptor, and a mechanical stirrer, 200 g of Maleination Reaction 2 product and 30 g of methyl-2-aminobenzoate, a UV-B absorber, were mixed and heated to 80° C. and held for 19 hours.

Example 3

Grafting a UV-A Absorber onto Maleated Soybean Oil (with Initiator)

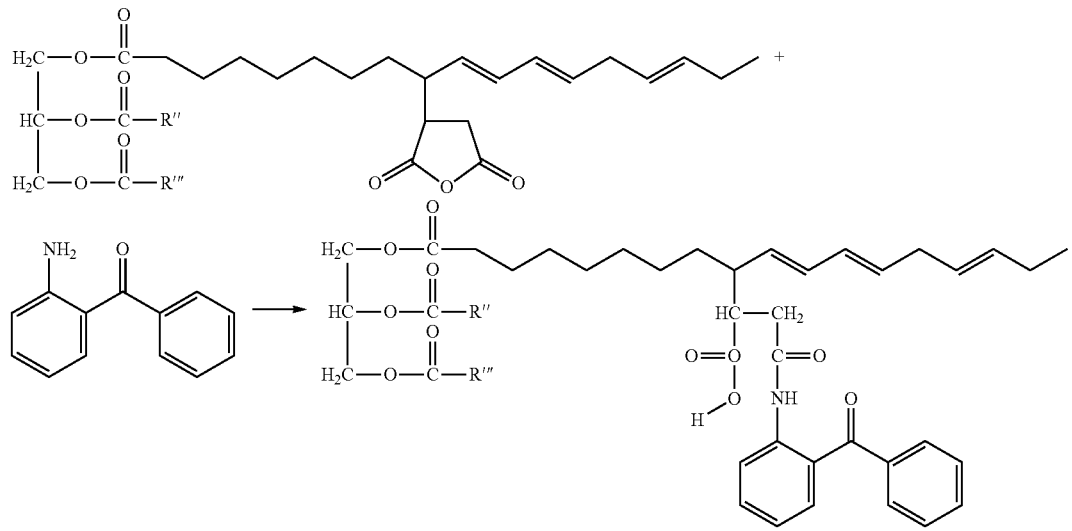

R″ and R‴ are alkyl or alkenyl groups that naturally occur in soybean oil.

In a 1-L, 4-necked kettle equipped with a thermocouple, a condenser, a nitrogen purge adaptor, and a mechanical stirrer, 200 g of Maleination Reaction 2 product and 36 g of 2-aminobenzophenone, a UV-A absorber, were mixed and heated to 130° C. and held for 40 hours.

Example 4

Grafting UV-A and UV-B Absorbers onto Maleated Soybean Oil (with Initiator)

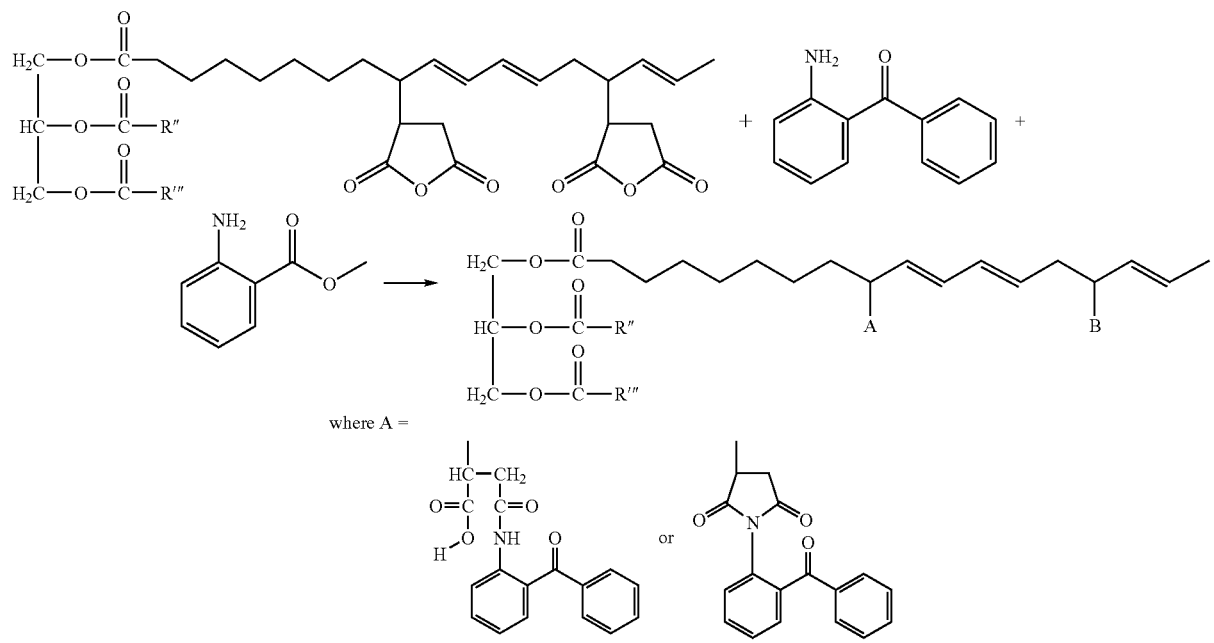

where B =

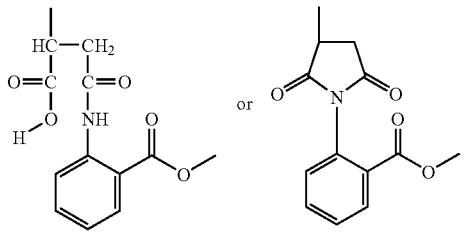

R" and R'" are alkyl or alkenyl groups that naturally occur in soybean oil.

In a 1-L, 4-necked kettle equipped with a thermocouple, a condenser, a nitrogen purge adaptor, and a mechanical stirrer, 200 g of Maleination Reaction 2 product, 26.9 g of 2-aminobenzophenone (a UV-A absorber), and 20.6 g of methyl 2-aminobenzoate (a UV-B absorber) were mixed and heated to 130° C. and held for 48 hours.

Example 5

Grafting UV-A and UV-B Absorbers onto Maleated Soybean Oil (with Initiator)

Example 4 was repeated, but after mixing the reactants they were heated to 80° C. and held for 48 hours.

Example 6

Example 4 was repeated, but after mixing the reactants they were heated to 170° C. and held for 72 hours.

Maleination Reaction 3

Grafting Maleic Anhydride onto Soybean Oil without Initiator

In a 1-L, 4-necked kettle equipped with a thermocouple, a condenser, a nitrogen purge adaptor, and a mechanical stirrer, 200 g soybean oil were charged. The mixture was slowly heated for 30 minutes from room temperature (about 22° C.) to 210° C. Then, 60 g of maleic anhydride were charged and the mixture was held isothermally at 210° C. After 1.5 hours, another 60 g charge of maleic anhydride was fed to the reactor, and the reactor was held isothermally at 210° C. for about 5-6 hours. Completion of the reaction was indicated when a drop of the reacting solution did not turn triphenylphosphine test paper orange-red.

Example 7

Grafting UV-B Absorber onto Maleated Soybean Oil (with Initiator)

In a 1-L, 4-necked kettle equipped with a thermocouple, a condenser, a nitrogen purge adaptor, and a mechanical stirrer, 100 g of product from Maleination Reaction 3 and 56.6 g of methyl 2-aminobenzoate were mixed and heated to 130° C. and held for 54 hours.

Example 8

Grafting UV-A Absorber onto Maleated Soybean Oil (with Initiator)

In a 1-L, 4-necked kettle equipped with a thermocouple, a condenser, a nitrogen purge adaptor, and a mechanical stirrer, 50 g of product from Maleination Reaction 3 and 68 g of 2-aminobenzophenone were mixed and heated to 130° C. and held for 42 hours.

The invention has been described in detail with particular reference to preferred embodiments thereof, but it will be understood that variations and modifications can be effected within the spirit and scope of the invention.

What is claimed is:

1. A UV-absorbing compound derived from at least: (a) a UV absorber having at least one hydroxyl group, primary amine group, or secondary amine group, (b) a coupling agent having anhydride functionality, and (c) a graft host comprising an unsaturated fatty acid.

2. The compound of claim 1 wherein said UV absorber exhibits at least one of UV-A or UV-B activity.

3. The compound of claim 2 wherein said UV-A or UV-B absorber is selected from the group consisting of: aminobenzoic acid; 2-aminobenzophenone; amyl dimethyl PABA; bemotrizinol; benzophenone-3; benzophenone-4; benzophenone-9; 2-(2H-benzotriazole-2-yl)-4,6-di-tert-pentylphenol; 2-(2H-benzotriazole-2-yl)-4-methylphenol; 2-(2H-benzotriazole-2-yl)-4,6-bis(1-methyl-1-phenylethyl)phenol; bis-benzoxazoyl phenyl ethylhexyl amino triazine; 3-benzylidene camphor sulfonic acid; N,N'-bisformyl-N,N-bis-(2,2,6,6-tetramethyl-4-piperidinyl)-hexamethylendi-amine; bisoctrizole; 2-[p-(tert-butylamido)-anilino]-4,6,-bis[(p-(2'-ethylhexyl-1'-oxycarbony-1)-anilino]-1,3,5-triazine; 6-tert-butyl-2-(5-chloro-2H-benzotriazole-2-yl)-4-methylphenol; 2,4-di-tert-butyl-6-(5-chloro-2H-benzotriazole-2-yl)-phenol; camphor benzalkonium methosulfate; diethanolamine p-methoxycinnamate; diethylaminohydroxybenzoyl-hexylbenzoate; diethylhexyl butamido triazone; digalloyl trioleate; dioxybenzone; disodium phenyl dibenzimidazole tetrasulfonate; drometrizole trisiloxane; ecamsule; ensulizole; ethyl 4-bis(hydroxypropyl)aminobenzoate; ethylhexyl p-methoxycinnamate; 2-ethylhexyl salicylate; ethylhexyl triazone; beta-2-glucopyranoxypropylhydroxy-benzophenone; glyceryl aminobenzoate; homomethyl salicylate; [2-hydroxy-4-(octyloxy)phenyl](phenyl)methanone; 2-[bis(2-hydroxyethyl)amino]ethyl salicylate; (E)-3-(4-hydroxy-3-methoxyphenyl)prop-2-enoic acid; lawsone with dihydroxyacetone; meradimate; methoxycinnamido propyl hydroxy sultaine menthyl anthranilate; meradimate; methyl-2-aminobenzoate; oxybenzone; 2-phenylbenzimidazole-5-sulfonic acid (and its potassium, sodium and triethanolamine salts); sulisobenzone; bis-(2,2,6,6-tetramethyl-4-piperidyl)-sebacate; sterically hindered oligomeric amine; triethanolamine salicylate; N-(2-ethoxyphenyl)-N-(2-ethylphenyl)oxamide; 4-methylhexyl 3-(3-benzotriazol-2-yl-4-hydroxy-5-tert-butyl-phenyl)propanoate; and blends thereof.

4. A composition comprising from about 0.01% to about 100% of said UV-absorbing compound of claim 1.

5. The composition of claim 4 that additionally comprises at least one ingredient selected from the group consisting of:

actives, adhesives, anti-oxidants, binders, biocides, colorants, defoamers, dyes, emollients, fragrances, humectants, labile UV absorbers, lubricants, oils, pigments, preservatives, propellants, surfactants, thickeners, water, waxes, and blends thereof.

6. The composition of claim 4 that is a personal care composition or a performance chemicals composition.

7. The performance chemicals composition of claim 6 that is an adhesive, agricultural, cleaning, coating, construction material, encapsulation, ink, membrane, printing, plastic, or packaging composition.

* * * * *